(12) United States Patent
Zeng

(10) Patent No.: US 11,607,257 B2
(45) Date of Patent: Mar. 21, 2023

(54) HIGH-STRENGTH ABSORBABLE INTERNAL FIXATION BONE SCREW FOR FRACTURE

(71) Applicants: LANZHOU SEEMINE SMA CO., LTD, Lanzhou (CN); SUZHOU SEEMINE-NEBULA BIOTECHNOLOGY CO., LTD, Suzhou (CN)

(72) Inventor: Chenguang Zeng, Guangzhou (CN)

(73) Assignee: SUZHOU SEEMINE-NEBULA BIOTECHNOLOGY CO., LTD, Suzhou (CN)

( * ) Notice: Subject to any disclaimer, the term of this patent is extended or adjusted under 35 U.S.C. 154(b) by 975 days.

(21) Appl. No.: 16/462,486

(22) PCT Filed: Dec. 14, 2017

(86) PCT No.: PCT/CN2017/116143
§ 371 (c)(1),
(2) Date: May 20, 2019

(87) PCT Pub. No.: WO2018/113579
PCT Pub. Date: Jun. 28, 2018

(65) Prior Publication Data
US 2019/0365443 A1    Dec. 5, 2019

(30) Foreign Application Priority Data

Dec. 19, 2016   (CN) .......................... 201611178598.9

(51) Int. Cl.
*A61B 17/86* (2006.01)
*A61L 31/06* (2006.01)
(Continued)

(52) U.S. Cl.
CPC ........ *A61B 17/866* (2013.01); *A61B 17/8625* (2013.01); *A61B 17/8665* (2013.01);
(Continued)

(58) Field of Classification Search
CPC . A61B 17/686; A61B 17/7002; A61B 17/663; A61B 17/866
See application file for complete search history.

(56) References Cited

U.S. PATENT DOCUMENTS

| 6,232,384 B1* | 5/2001 | Hyon .................... A61L 31/127 524/415 |
| 2005/0182411 A1 | 8/2005 | DeMeo et al. |
| 2005/0288673 A1* | 12/2005 | Catbagan ............. A61B 17/701 606/279 |

FOREIGN PATENT DOCUMENTS

| CN | 1306802 A | 8/2001 |
| CN | 102266593 A | 12/2011 |

(Continued)

*Primary Examiner* — Jason-Dennis N Stewart
(74) *Attorney, Agent, or Firm* — Muncy, Geissler, Olds & Lowe, P.C.

(57) ABSTRACT

A high-strength absorbable internal fixation bone screw for a fracture. The bone screw is made of a degradable oriented polylactic acid section. A raw material for the oriented polylactic acid section is a poly(L-lactic acid). The specific optical rotation of the poly(L-lactic acid) is −155° to −160°. The section is made of the poly(L-lactic acid) through the processes of making a billet, orientation strengthening and quenching in order. The method for making the billet is plastic injection molding. The method for orientation strengthening is forging and pressing or extrusion. The section is turned, finely milled, or directly molded into the bone screw. The bone screw has high strength and a low rate of mechanical strength loss, ensures mechanical support during bone healing and sufficient healing time for an injured bone, has good biocompatibility, and can be degraded and absorbed.

12 Claims, 2 Drawing Sheets

(51) Int. Cl.
  *A61L 31/14*  (2006.01)
  *B29C 71/02*  (2006.01)
  *A61B 17/00*  (2006.01)
  *B29K 67/00*  (2006.01)
  *B29L 31/00*  (2006.01)

(52) U.S. Cl.
  CPC ............ *A61L 31/06* (2013.01); *A61L 31/148* (2013.01); *B29C 71/02* (2013.01); *A61B 2017/00004* (2013.01); *B29C 2071/025* (2013.01); *B29K 2067/046* (2013.01); *B29L 2031/753* (2013.01)

(56) References Cited

FOREIGN PATENT DOCUMENTS

| | | |
|---|---|---|
| CN | 102490308 A | 6/2012 |
| CN | 104511056 A | 4/2015 |
| CN | 205458850 U | 8/2016 |
| CN | 106398148 A | 2/2017 |
| CN | 106691567 A | 5/2017 |
| CN | 106730043 A | 5/2017 |
| CN | 106823018 A | 6/2017 |
| EP | 0 146 398 A2 | 6/1985 |
| KR | 10-0383433 B1 | 5/2003 |

\* cited by examiner

HIGH-STRENGTH ABSORBABLE INTERNAL FIXATION BONE SCREW FOR FRACTURE

CROSS REFERENCE TO RELATED APPLICATIONS

This application is the national phase entry of International Application No. PCT/CN2017/116143 under the china priority 201611178598.9, filed on Dec. 14, 2017, the entire contents of which are incorporated herein by reference.

TECHNICAL FIELD

The present invention belongs to the field of medical surgical instruments, and particularly relates to a high-strength absorbable internal fixation bone screw for a fracture.

BACKGROUND OF THE INVENTION

Polylactic acid is a fully degradable absorbent material with good biocompatibility, can be degraded into lactic acid in vivo to enter a tricarboxylic acid cycle, can be finally produced into $CO_2$ and $H_2O$, is non-toxic and harmless to the human body, and is one of synthetic degradable polymers mostly applied to medicine currently. The polylactic acid is widely applied to drug sustained-release materials, implant materials in vivo, surgical sutures, orthopedic internal fixation materials, tissue engineering materials, and the like in the medical field.

Broken bones of the human body or animal body can be combined by means of internal fixation devices. A screw internal fixation technology has been used to treat fractures for over 100 years. The technology adopts various screws, such as ordinary screws, screws with different thread pitches and screw rods, hollow screws, hip screws, expansion screws, double-thread screws, locking screws, micrometer screws, and even some screws (such as pedicle screws) for specific parts, or screws made of special materials (such as absorbable screws). The screw can be used alone or can also be used as an essential part for matching with other various fixation systems (such as a screw-plate system or an intramedullary nail system). With the improvement of the concepts and technologies of fracture trauma diagnosis and treatment, the requirements for the manufacturing and processing technologies of internal fixation instruments are constantly updated, and the forms and functions of the screws are also greatly changed. The existing bone screws are mainly made of a polylactic acid material consisting of D-lactic acid and trimethylene carbonate. However, for a bone screw made of the polylactic acid material consisting of D-lactic acid or trimethylene carbonate, a racemate D,D-polylactic acid (PDLA) synthesized by racemic poly(D-lactic acid) is of an amorphous structure, so that the bone screw has poor mechanical properties and shorter degradation time, cannot keep sufficient time and sufficient strength in the human body, and results in insufficient healing time for a bone fracture of a patient and a hidden trouble.

SUMMARY OF THE INVENTION

The present invention is directed to a high-strength absorbable internal fixation bone screw for a fracture so as to overcome the defects of the prior art.

In order to achieve the above objective, the present invention adopts the following technical solution: a high-strength absorbable internal fixation bone screw for a fracture is disclosed, the bone screw is made of an oriented polylactic acid section, a raw material for the oriented polylactic acid section is a poly(L-lactic acid), the specific optical rotation of the poly(L-lactic acid) is −155° to −160°, the crystallinity of the section is 45% to 85%, and the bending strength of the bone screw is 200 MPa to 450 MPa.

Preferably, the oriented polylactic acid section is made of the poly(L-lactic acid) through the processes of making a billet, orientation strengthening and quenching in order, where a method for making the billet is plastic injection molding, and a method for orientation strengthening is forging and pressing or extrusion.

Preferably, the temperature for making the billet is 180° C. to 220° C., the temperature for extrusion strengthening in the orientation strengthening method is 130° C. to 180° C., the temperature for forging and pressing strengthening is 160° C. to 190° C., the quenching rate is 60° C./min to 140° C./min, and the quenching time is 1 min to 2 min.

Preferably, the bone screw is made of the oriented polylactic acid section by a turning method, a fine milling method, or a direct molding method.

Preferably, in the turning method, a two-way linkage clamp is used for clamping two ends of the oriented polylactic acid section so as to turn a middle part of the oriented polylactic acid section.

Preferably, in the fine milling method, a graded clamp is used for performing graded clamping and processing on the oriented polylactic acid section.

Preferably, in the direct molding method, the made billet is directly molded into a bar with a thread in a mold cavity through an extrusion strengthening technology, and then, other parts of the bar are turned or finely milled.

Preferably, the bone screw is composed of a nut and a screw rod segment, a top end of the nut has a spherical surface, a middle part of the nut is cylindrical, and a tail end of the nut has a chamfer; and a spherical surface of the top end of the nut is provided with a groove, and the groove is in one of a cross shape, a linear shape and an internal hexagonal shape.

Preferably, a thread of the screw rod segment is one of a rectangular thread, a triangular thread, a trapezoidal thread or a saw-tooth thread.

Preferably, a connecting part is arranged between an upper end of the thread of the screw rod segment and a tail end of the nut, and an end surface of the tail end of the screw rod segment has a chamfer.

The present invention has the following beneficial effects:

1. The high-strength absorbable internal fixation bone screw for a fracture, provided by the present invention, is made of the oriented polylactic acid section, the oriented polylactic acid section is made of the poly(L-lactic acid) through processes of making the billet, orientation strengthening and quenching in order. The bone screw made of the oriented polylactic acid section through stamping and machining has high strength. After the bone screw is implanted for 18-36 weeks, the implant gradually loses strength, thereby ensuring that a bone does not deform during healing. The bone screw generates biological reabsorption in 2-4 years, so that the bone screw has good biocompatibility and ensures sufficient healing time for an injured bone.

2. The high-strength absorbable internal fixation bone screw for a fracture has a low rate of mechanical strength loss and can ensure sufficient mechanical support in a healing stage. With degradation of the bone screw, the stress is gradually transferred to a healed fracture surface. By means of increase of the bone density, osteoporosis can be reduced, and the effect on fixation of a cancellous bone fracture is obvious. Under special conditions, the size of the bone screw can be adjusted according to the osteotomy of ankles, the fracture degree of ankle joints, and the characteristics of growth plates of ulnas.

DETAILED DESCRIPTION

Figure 1:
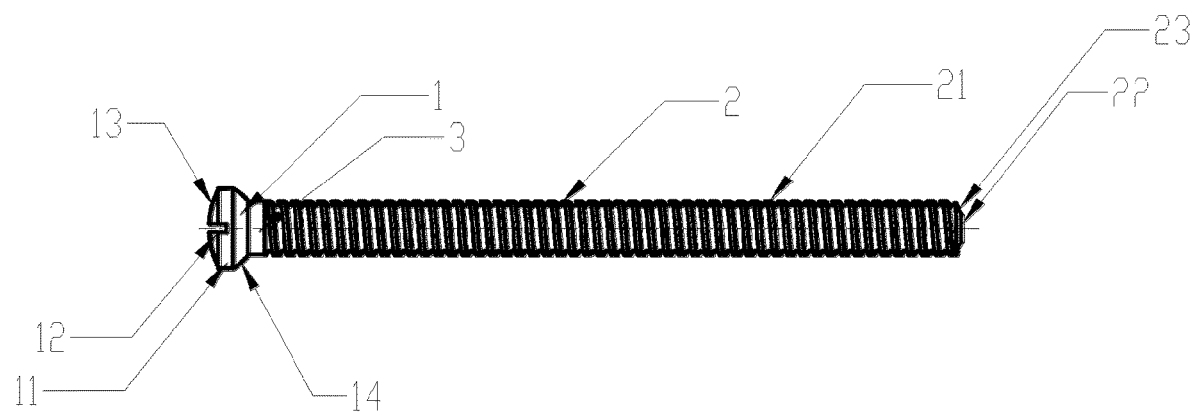
FIG. 1 is a structural schematic diagram of a preferred embodiment of a bone screw in a high-strength absorbable internal fixation component of the present invention.

A specific embodiment of the present invention is further described below in conjunction with the accompanying drawings:

The present invention provides a high-strength absorbable internal fixation bone screw for a fracture. The bone screw is made of an oriented polylactic acid section, a raw material for the oriented polylactic acid section is a poly(L-lactic acid), and the specific optical rotation of the poly(L-lactic acid) is −155° to −160°. The oriented polylactic acid section is made of the poly(L-lactic acid) through the processes of making a billet, orientation strengthening and quenching in order, where a method for making the billet is plastic injection molding, and a method for orientation strengthening is forging and pressing or extrusion. The crystallinity of the section is 45% to 85%.

In the making process of the oriented polylactic acid section of the present invention, the temperature for making the billet is 180° C. to 220° C., the temperature for extrusion strengthening is 130° C. to 180° C., the temperature for forging and pressing strengthening is 160° C. to 190° C., the quenching rate is 60° C./min to 140° C./min, and the quenching time is 1 min to 2 min.

In the processing process of the bone screw of the present invention, the section obtained by strengthening has high toughness, large processing difficulty and low efficiency, so the present invention provides the following three processing technologies to improve the processing efficiency and stability:

a turning method: a two-way linkage clamp is used for clamping two ends of the section so as to turn a middle part of the section, thereby preventing the section from shaking in the making process;

a fine milling method: a graded clamp is used for performing graded clamping on the section so as to shorten the processing length, thereby improving the stability of the section; and a direct molding method: the made billet is directly extruded and molded into a bar with a thread in a mold cavity through an extrusion strengthening technology, and then, other parts of the bar are turned or finely milled.

The bone screw made of the oriented polylactic acid section through extrusion strengthening and machining has high strength. In this embodiment, the maximum bending strength can reach 420 MPa. The bone screw has a low rate of mechanical strength loss. After the bone screw is implanted for 18-36 weeks, the implant gradually loses strength, thereby ensuring sufficient mechanical support in a healing stage. The bone screw generates biological reabsorption in 2-4 years, so that the bone screw ensures sufficient healing time for an injured bone.

The bone screw of the present invention is composed of a nut and a screw rod segment, and the length of the bone screw is 37 to 43 mm. The height of the nut is 1.8 to 2.2 mm, the diameter of the nut is 4.0 to 4.6 mm, the chamfer radius of a spherical surface of a top end of the nut is 4.6 to 5.0 mm, the height of a middle part of the nut is 0.6 to 1.0 mm, and the chamfer radius of a tail end of the nut is 2.5 to 2.9 mm. The spherical surface of the top end of the nut is provided with a groove, the groove is in one of a cross shape, a linear shape and an internal hexagonal shape, the width of the groove is 0.2 to 0.6 mm, and the depth of the groove is 0.7 to 1.1 mm. A thread of the screw rod segment is one of a rectangular thread, a triangular thread, a trapezoidal thread and a saw-tooth thread. The external diameter of the thread is 2.6 to 3.0 mm, the thread pitch is 0.5 to 0.9 mm, the vertical distance between a root of the thread and a crest of the thread is 0.1 to 0.3 mm, an opening angle between two adjacent threads is 50° to 60°, and the fillet radius of the root of the thread is 0.2 mm. The height of a connecting part between an upper end of the thread of the screw rod segment and the nut is 0.6 to 1.0 mm, the diameter of an end surface of a tail end of the screw rod segment is 1.3 to 1.5 mm, and the angle of a chamfer of the tail end is 120° to 130°. The diameter of a screw hole in a fixed bone plate used together with the bone screw is smaller than the diameter of the nut and greater than the external diameter of the thread of the screw rod.

Figure 2:
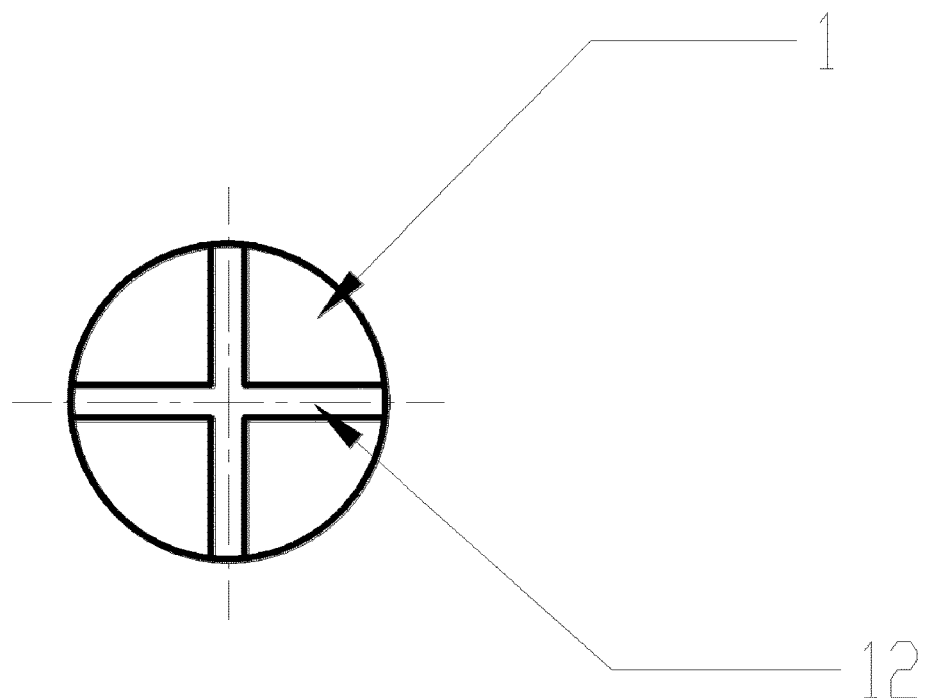
FIG. 2 is a schematic diagram of a preferred embodiment of a groove in a top end of a nut of the bone screw in the high-strength absorbable internal fixation component of the present invention.
Figure 3:
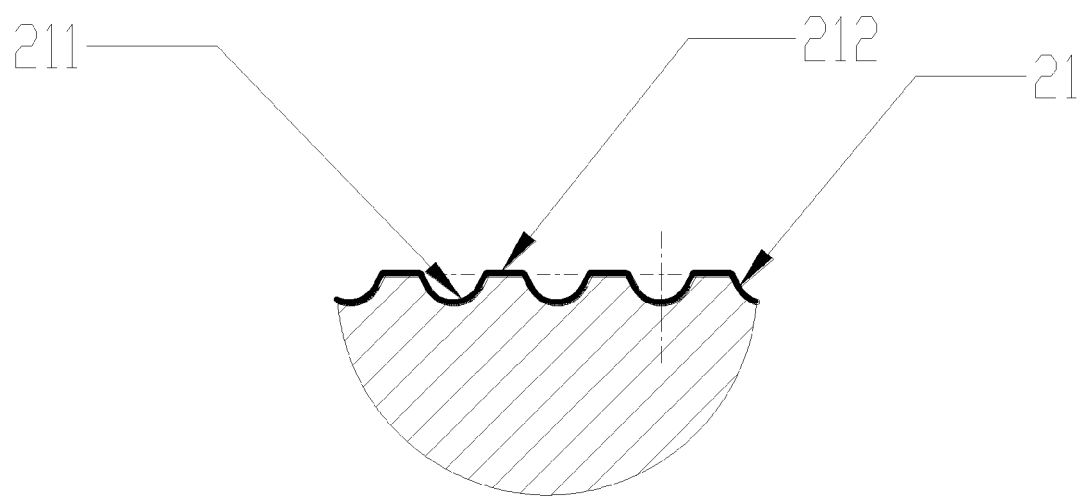
FIG. 3 is a partial schematic diagram of a preferred embodiment of a thread of the bone screw in the high-strength absorbable internal fixation component of the present invention.

A preferred solution of the present invention is shown in FIG. 1 to FIG. 3.

Referring to FIG. 1, in this embodiment, the bone screw is composed of a nut 1 and a screw rod segment 2, and the length of the bone screw is preferably 40 mm. The height of the nut 1 is 2 mm, the diameter of the nut 1 is 4.2 mm, the chamfer radius of a spherical surface 13 of the top end of the nut 1 is 4.8 mm, the height of a middle part 11 of the nut 1 is 0.8 mm, and the chamfer radius of a tail end 14 of the nut 1 is 2.7 mm. Referring to FIG. 1 and FIG. 2, the spherical surface 13 of the top end of the nut 1 is provided with a groove 12, the groove 12 is preferably in a cross shape, the width of the groove 12 is 0.4 mm, and the depth of the groove 12 is 0.9 mm. Referring to FIG. 1 and FIG. 3, a thread 21 of the screw rod segment 2 is preferably a trapezoidal thread, the external diameter of the thread 21 is 2.8 mm, the thread pitch is 0.7 mm, the vertical distance between a root 211 of the thread 21 and a crest 212 of the thread 21 is 0.2 mm, an opening angle between two adjacent threads is 54°, and the fillet radius of the root 211 of the thread 21 is 0.2 mm. The height of a connecting part 3 between an upper end of the thread 21 of the screw rod segment 2 and the nut 1 is 0.8 mm, the diameter of an end surface 22 of a tail end of the screw rod segment 2 is 1.4 mm, and the angle of a chamfer 23 of the tail end is 125°.

According to the disclosure and teaching of the above specification, a person skilled in the art to which the present invention belongs can also make changes and modifications to the above embodiment. Therefore, the present invention is not limited to the specific embodiment disclosed and described above, and some modifications and changes of the present invention shall also fall within the protection scope of the claims of the present invention. In addition, although some specific terms are used in the specification, these terms are merely for convenience of description and do not limit the present invention.

What is claimed is:

1. A high-strength absorbable internal fixation bone screw for a fracture, wherein the bone screw is made of an oriented polylactic acid section, a raw material for the oriented polylactic acid section is only a poly(L-lactic acid), the specific optical rotation of the poly(L-lactic acid) is −155° to −160°, the crystallinity of the section is 45% to 85%, and the bending strength of the bone screw is 200 MPa to 450 MPa.

2. The high-strength absorbable internal fixation bone screw for a fracture according to claim 1, wherein the oriented polylactic acid section is made of the poly(L-lactic acid) through processes of making a billet, orientation strengthening and quenching in order, wherein a method for making the billet is plastic injection molding, and a method for orientation strengthening is forging and pressing or extrusion.

3. The high-strength absorbable internal fixation bone screw for a fracture according to claim 2, wherein the temperature for making the billet is 180° C. to 220° C., the temperature for extrusion strengthening in the orientation strengthening method is 130° C. to 180° C., the temperature for forging and pressing strengthening is 160° C. to 190° C., the quenching rate is 60° C/min to 140° C/min, and the quenching time is 1 min to 2 min.

4. The high-strength absorbable internal fixation bone screw for a fracture according to claim 2, wherein in the direct molding method, the made billet is directly molded into a bar with a thread in a mold cavity through an extrusion strengthening technology, and then, other parts of the bar are turned or finely milled.

5. The high-strength absorbable internal fixation bone screw for a fracture according to claim 1, wherein the bone screw is made by a turning method, a fine milling method, or a direct molding method.

6. The high-strength absorbable internal fixation bone screw for a fracture according to claim 5, wherein in the turning method, a two-way linkage clamp is used for clamping two ends of the oriented polylactic acid section so as to turn a middle part of the oriented polylactic acid section.

7. The high-strength absorbable internal fixation bone screw for a fracture according to claim 5, wherein in the fine milling method, a graded clamp is used for performing graded clamping and processing on the oriented polylactic acid section.

8. The high-strength absorbable internal fixation bone screw for a fracture according to claim 5, wherein in the direct molding method, the made billet is directly molded into a bar with a thread in a mold cavity through an extrusion strengthening technology, and then, other parts of the bar are turned or finely milled.

9. The high-strength absorbable internal fixation bone screw for a fracture according to claim 1, wherein the bone screw is composed of a nut and a screw rod segment, the top end of the nut has a spherical surface, a middle part of the nut is cylindrical, and a tail end of the nut has a chamfer; and the spherical surface of the top end of the nut is provided with a groove, and the groove is in one of a cross shape, a linear shape and an internal hexagonal shape.

10. The high-strength absorbable internal fixation bone screw for a fracture according to claim 9, wherein a thread of the screw rod segment is one of a rectangular thread, a triangular thread, a trapezoidal thread or a saw-tooth thread.

11. The high-strength absorbable internal fixation bone screw for a fracture according to claim 10, wherein a connecting part is arranged between an upper end of the thread of the screw rod segment and the tail end of the nut, and an end surface of the tail end of the screw rod segment has a chamfer.

12. The high-strength absorbable internal fixation bone screw for a fracture according to claim 9, wherein a connecting part is arranged between an upper end of the thread of the screw rod segment and the tail end of the nut, and an end surface of the tail end of the screw rod segment has a chamfer.

* * * * *